US006824989B1

(12) United States Patent
Eisinger et al.

(10) Patent No.: US 6,824,989 B1
(45) Date of Patent: Nov. 30, 2004

(54) RECOMBINANT MONOCLONAL ANTIBODY TO PHOSPHOTYROSINE-CONTAINING PROTEINS

(75) Inventors: Dominic Eisinger, Keene, NY (US); Lynn Stiles, Saranac Lake, NY (US); Arthur LaMarche, Lake Placid, NY (US); Thomas Jelinek, Lake Placid, NY (US)

(73) Assignee: Upstate Biotechnology, Inc., Lake Placid, NY (US)

( * ) Notice: Subject to any disclaimer, the term of this patent is extended or adjusted under 35 U.S.C. 154(b) by 672 days.

(21) Appl. No.: 09/653,755

(22) Filed: Sep. 1, 2000

(51) Int. Cl.$^7$ .............................................. G01N 33/53
(52) U.S. Cl. .................... 435/7.1; 435/6; 435/91.1; 435/69.1; 435/325; 435/320; 530/387.3
(58) Field of Search ........................... 435/7.1, 6, 91.1, 435/69.1, 325, 320, 252.3; 530/387.3

(56) References Cited

U.S. PATENT DOCUMENTS

| 5,731,427 A | * | 3/1998 | Wong et al. ............... 536/23.5 |
| 5,736,381 A | * | 4/1998 | Davis et al. ............. 435/252.3 |
| 2002/0025540 A1 | * | 2/2002 | Roberts et al. ............. 435/7.9 |

FOREIGN PATENT DOCUMENTS

WO    WO 97 42501 A    11/1997

OTHER PUBLICATIONS

Biochemistry 29(37): 8509–8517.*
Trends in Genetics 15(4): 132–133.*
Trends in Genetics 12(10) 425–427.*
Trends in Biotech. 18(1): 34–39.*
Flier, et al., "Oncogenes, Growth Factors, and Signal Transduction," Seminars in Medicine of the Beth Israel Hospital, vol. 321, No. 20, pp. 1383–1391 (Nov. 1989).
Kanakura, et al., "Signal Transduction of the Human Granulocyte–Macrophage Colony–Stimulating . . . ," Blood, vol. 76, No. 4, pp. 706–715 (Aug. 15).
Morrison, et al., "Tyrosine Phosphorylations in Vivo Associated with v–fms Transformation," Molecular and Cellular Biology, pp. 176–185 (Jan. 1988).
Ward, et al., "Regulation of Phosphoinositide Kinases in T Cells," The Journal of Biological Chemistry, vol. 267, No. 33, pp. 23862–23869 (Nov. 1992).
Cohen, et al., "Tyrosine phosphorylation is a signal for the Trafficking of pp85, and 85–kDa phosphorylated polypeptide associated with phosphatidylinositol kinase activity," Proc. Nat'l, Acad. Sci., vol. 87, pp. 4458–4462 (Jun. 1990).
Wegener, Anne–Marie Karin, et al, "Distinct domains of the CD3–gamma chain are involved in surface expression and function of the T cell antigen receptor.", Journal of Biological Chemistry, vol. 270 No. 9, 1995, pp. 4675–4680.
Sunanda, R. Narayanan, "Preparative Affinity Chromatography of Proteins", Journal of Chromatography A, Elsevier Science, NL, vol. 658 No. 2, Jan. 14, 1994, pp. 237–258.
Kanakura, Y, et al, "Phorbol 12–Myristate 13–Acetate Inhibits Granulocyte–Macrophage Colony Stimulating Factor–Induced Protein Tyrosine Phosphorylation in Human Factor–Dependent Hematopoietic Cell Line", Journal of Biological Chemistry, vol. 266, No. 1, 1991, pp. 490–495.
Jean, Yin Jen Wang, "Antibodies for Phosphotyrosine: Analytical and Preparative Tool Fortyrosyl–Phosphorylated Proteins", Analytical Biochemistry, vol. 172, 1988, pp. 1–7.
Mayer, A, et al, "Exemplifying guidelines for preparation of recombinant DNA products in phase I trails in cancer: Preparation of a genetically engineered anti–CEA single chain Fv antibody", European Journal of Cancer, vol. 34, No. 7, Jun. 1998 (1998–96), pp. 968–976.
Trill, John J, et al, "Production of monoclonal antibodies in COS and CHO cells", Current Opinion in Biotechnology, vol. 6, No. 5, 1995, pp. 553–560.

* cited by examiner

Primary Examiner—Bao-Thuy L. Nguyen
Assistant Examiner—Changhwa J Cheu
(74) Attorney, Agent, or Firm—Elliot M. Olstein; Alan J. Grant

(57) ABSTRACT

A purified or highly pure recombinant monoclonal antibody with 4G10-hybridoma type specificity is disclosed along with polynucleotides, including cDNA sequences, encoding the antibody chains and the amino acid sequences corresponding to said cDNA polynucleotides and uses for said sequences. Also disclosed are corresponding tagged sequences useful in molecular biological techniques and uses for said sequences.

7 Claims, 5 Drawing Sheets

Fig. 3

SEQUENCE LISTING

<160> NUMBER OF SEQ ID NOS: 12

<210> SEQ ID NO 1
<211> LENGTH: 1365
<212> TYPE: DNA
<213> ORGANISM: Artificial Sequence
<220> FEATURE:
<223> OTHER INFORMATION: Description of Artificial Sequence:cDNA for heavy chain of recombinant antibody

<400> SEQUENCE: 1

```
gaggtccagc tgcarcagtc tggacctgaa ctggtgaagc tggggcttc agtgatgata        60
tcctgcagga cttctgcata cacattcact gaaaacaccg tgcactgggt gaagcagagc       120
catggagaga gccttgagtg gattggaggt attaatcctt actatggtgg ttctatcttc       180
agcccgaagt tcaagggcaa ggccacattg actgtagaca agtcctccag cacagcctac       240
atggagctcc gcagcctgac atctgaggat tctgcagtct attactgtgc aagaagggct       300
ggggcgtact actttgacta ctggggccaa ggcaccactc tcacagtctc ctcagccaaa       360
acaacacccc catcagtcta tccactggcc cctgggtgtg agatacaac tggttcctcc        420
gtgactctgg gatgcctggt caagggctac ttccctgagt cagtgactgt gacttggaac       480
tctggatccc tgtccagcag tgtgcacacc ttcccagctc cctgcagtc tggactctac        540
actatgagca gctcagtgac tgtcccctcc agcacctggc caagtcagac cgtcacctgc       600
agcgttgctc acccagccag cagcaccacg gtggacaaaa acttgagcc cagcgggccc        660
atttcaacaa tcaaccctg tcctccatgc aaggagtgtc acaaatgccc agctcctaac        720
ctcgagggtg gaccatccgt cttcatcttc cctccaaaata tcaaggatgt actcatgatc      780
tccctgacac ccaaggtcac gtgtgtggtg gtggatgtga gcgaggatga cccagacgtc       840
cagatcagct ggtttgtgaa caacgtggaa gtacacacag ctcagacaca aacccataga       900
gaggattaca acagtactat ccgggtggtc agcaccctcc ccatccagca ccaggactgg       960
atgagtggca aggagttcaa atgcaaggtc aacaacaaag acctcccatc acccatcgag      1020
agaaccatct caaaaattaa agggctagtc agagctccac aagtatacat cttgccgcca      1080
ccagcagagc agttgtccag gaaagatgtc agtctcactt gcctggtcgt gggcttcaac      1140
cctggagaca tcagtgtgga gtggaccagc aatgggcata cagaggagaa ctacaaggac      1200
accgcaccag tcctggactc tgacggttct tacttcatat atagcaagct caatatgaaa      1260
acaagcaagt gggagaaaac agattccttc tcatgcaacg tgagacacga gggtctgaaa      1320
aattactacc tgaagaagac catctcccgg tctccgggta atga                      1365
```

<210> SEQ ID NO 2
<211> LENGTH: 645
<212> TYPE: DNA
<213> ORGANISM: Artificial Sequence
<220> FEATURE:
<223> OTHER INFORMATION: Description of Artificial Sequence:cDNA for light chain of recombinant antibody

<400> SEQUENCE: 2

```
gaaaatgtgc tcacccagtc tccagcaatc atgtctgcat ctccagggga aaaggtcacc        60
atgacctgca gggccagctc aagtgtaagt tccagttact tgcactggta tcggcagaag       120
tcaggtgcct cccccaaact ctggatttat agcacatcca acttggcttc tggagtccct       180
gctcgcttca gtggcagtgg gtctgggacc tcttactctc tcacaatcag cagtgtggag       240
gctgaagatg ctgccactta ttactgccag cagtacagtg ttaccggac gttcggtgga       300
ggcaccaagc tggaaatcaa acgggctgat gctgcaccaa ctgtatccat cttcccacca      360
tccagtgagc agttaacatc tggaggtgcc tcagtcgtgt gcttcttgaa caacttctac       420
cccagagaca tcaatgtcaa gtggaagatt gatggcagtg aacgacaaaa tggtgtcctg      480
aacagttgga ctgatcagga cagcaaagac agcacctaca gcatgagcag caccctcaca      540
```

```
ttgaccaagg acgagtatga acgacataac agctatacct gtgaggccac tcacaagaca      600
tcaacttcac ccatcgtcaa gagcttcaac aggaatgagt gttag                      645
```

<210> SEQ ID NO 3
<211> LENGTH: 1389
<212> TYPE: DNA
<213> ORGANISM: Artificial Sequence
<220> FEATURE:
<223> OTHER INFORMATION: Description of Artificial Sequence:cDNA for
      heavy chain of recombinant antibody with 3'-histidine tag sequence

<400> SEQUENCE: 3

```
gaggtccagc tgcarcagtc tggacctgaa ctggtgaagc ctggggcttc agtgatgata      60
tcctgcagga cttctgcata cacattcact gaaaacaccg tgcactgggt gaagcagagc      120
catggagaga gccttgagtg gattggaggt attaatcctt actatggtgg ttctatcttc      180
agcccgaagt tcaagggcaa ggccacattg actgtagaca gtcctccag cacagcctac       240 atggagctcc gcagcctgac atctgaggat tctgcagtct attactgtgc aagaagggct      300
ggggcgtact actttgacta ctggggccaa ggcaccactc tcacagtctc ctcagccaaa      360
acaacacccc catcagtcta tccactggcc cctgggtgtg agatacaac tggttcctcc       420 gtgactctgg gatgcctggt caagggctac ttccctgagt cagtgactgt gacttggaac      480
tctggatccc tgtccagcag tgtgcacacc ttcccagctc tcctgcagtc tggactctac      540
actatgagca gctcagtgac tgtcccctcc agcacctggc caagtcagac cgtcacctgc      600
agcgttgctc acccagccag cagcaccacg gtggacaaaa acttgagcc cagcgggccc      660 atttcaacaa tcaaccctg tcctccatgc aaggagtgtc acaaatgccc agctcctaac       720
ctcgagggtg accatccgt cttcatcttc cctccaaata tcaaggatgt actcatgatc      780
tccctgacac ccaaggtcac gtgtgtggtg gtggatgtga gcgaggatga cccagacgtc      840
cagatcagct ggtttgtgaa caacgtggaa gtacacacag ctcagacaca aacccataga      900
gaggattaca acagtactat ccgggtggtc agcaccctcc ccatccagca ccaggactgg      960
atgagtggca aggagttcaa atgcaaggtc aacaacaaag acctcccatc acccatcgag      1020
agaaccatct caaaaattaa agggctagtc agagctccac aagtatacat cttgccgcca      1080
ccagcagagc agttgtccag gaaagatgtc agtctcactt gcctggtcgt gggcttcaac      1140
cctggagaca tcagtgtgga gtggaccagc aatgggcata cagaggagaa ctacaaggac      1200
accgcaccag tcctggactc tgacggttct tacttcatat atagcaagct caatatgaaa      1260
acaagcaagt gggagaaaac agattccttc tcatgcaacg tgagacacga gggtctgaaa      1320
aattactacc tgaagaagac catctcccgg tctccgggta aggtggcca tcaccaccat      1380 caccattga                                                              1389
```

<210> SEQ ID NO 4
<211> LENGTH: 454
<212> TYPE: PRT
<213> ORGANISM: Artificial Sequence
<220> FEATURE:
<223> OTHER INFORMATION: Description of Artificial Sequence:Amino acid
      sequence for heavy chain of recombinant antibody

<400> SEQUENCE: 4

```
Glu Val Gln Leu Gln Gln Ser Gly Pro Glu Leu Val Lys Pro Gly Ala
 1               5                  10                  15

Ser Val Met Ile Ser Cys Arg Thr Ser Ala Tyr Thr Phe Thr Glu Asn
            20                  25                  30
```

```
Thr Val His Trp Val Lys Gln Ser His Gly Glu Ser Leu Glu Trp Ile
         35                  40                  45

Gly Gly Ile Asn Pro Tyr Tyr Gly Gly Ser Ile Phe Ser Pro Lys Phe
 50                  55                  60

Lys Gly Lys Ala Thr Leu Thr Val Asp Lys Ser Ser Ser Thr Ala Tyr
 65                  70                  75                  80

Met Glu Leu Arg Ser Leu Thr Ser Glu Asp Ser Ala Val Tyr Tyr Cys
                 85                  90                  95

Ala Arg Arg Ala Gly Ala Tyr Tyr Phe Asp Tyr Trp Gly Gln Gly Thr
            100                 105                 110

Thr Leu Thr Val Ser Ser Ala Lys Thr Thr Pro Pro Ser Val Tyr Pro
        115                 120                 125

Leu Ala Pro Gly Cys Gly Asp Thr Thr Gly Ser Ser Val Thr Leu Gly
    130                 135                 140

Cys Leu Val Lys Gly Tyr Phe Pro Glu Ser Val Thr Val Thr Trp Asn
145                 150                 155                 160

Ser Gly Ser Leu Ser Ser Ser Val His Thr Phe Pro Ala Leu Leu Gln
                165                 170                 175

Ser Gly Leu Tyr Thr Met Ser Ser Ser Val Thr Val Pro Ser Ser Thr
            180                 185                 190

Trp Pro Ser Gln Thr Val Thr Cys Ser Val Ala His Pro Ala Ser Ser
        195                 200                 205

Thr Thr Val Asp Lys Lys Leu Glu Pro Ser Gly Pro Ile Ser Thr Ile
    210                 215                 220

Asn Pro Cys Pro Pro Cys Lys Glu Cys His Lys Cys Pro Ala Pro Asn
225                 230                 235                 240

Leu Glu Gly Gly Pro Ser Val Phe Ile Phe Pro Pro Asn Ile Lys Asp
                245                 250                 255

Val Leu Met Ile Ser Leu Thr Pro Lys Val Thr Cys Val Val Val Asp
            260                 265                 270

Val Ser Glu Asp Asp Pro Asp Val Gln Ile Ser Trp Phe Val Asn Asn
        275                 280                 285

Val Glu Val His Thr Ala Gln Thr Gln Thr His Arg Glu Asp Tyr Asn
    290                 295                 300

Ser Thr Ile Arg Val Val Ser Thr Leu Pro Ile Gln His Gln Asp Trp
305                 310                 315                 320

Met Ser Gly Lys Glu Phe Lys Cys Lys Val Asn Asn Lys Asp Leu Pro
                325                 330                 335

Ser Pro Ile Glu Arg Thr Ile Ser Lys Ile Lys Gly Leu Val Arg Ala
            340                 345                 350

Pro Gln Val Tyr Ile Leu Pro Pro Ala Glu Gln Leu Ser Arg Lys
        355                 360                 365

Asp Val Ser Leu Thr Cys Leu Val Val Gly Phe Asn Pro Gly Asp Ile
370                 375                 380

Ser Val Glu Trp Thr Ser Asn Gly His Thr Glu Glu Asn Tyr Lys Asp
385                 390                 395                 400

Thr Ala Pro Val Leu Asp Ser Asp Gly Ser Tyr Phe Ile Tyr Ser Lys
            405                 410                 415

Leu Asn Met Lys Thr Ser Lys Trp Glu Lys Thr Asp Ser Phe Ser Cys
        420                 425                 430
```

-continued

Asn Val Arg His Glu Gly Leu Lys Asn Tyr Tyr Leu Lys Lys Thr Ile
        435                 440                 445

Ser Arg Ser Pro Gly Lys
    450

<210> SEQ ID NO 5
<211> LENGTH: 214
<212> TYPE: PRT
<213> ORGANISM: Artificial Sequence
<220> FEATURE:
<223> OTHER INFORMATION: Description of Artificial Sequence:Amino acid
      sequence for light chain of recombinant antibody

<400> SEQUENCE: 5

Glu Asn Val Leu Thr Gln Ser Pro Ala Ile Met Ser Ala Ser Pro Gly
  1               5                  10                  15

Glu Lys Val Thr Met Thr Cys Arg Ala Ser Ser Val Ser Ser Ser
             20                  25                  30

Tyr Leu His Trp Tyr Arg Gln Lys Ser Gly Ala Ser Pro Lys Leu Trp
             35                  40                  45

Ile Tyr Ser Thr Ser Asn Leu Ala Ser Gly Val Pro Ala Arg Phe Ser
     50                  55                  60

Gly Ser Gly Ser Gly Thr Ser Tyr Ser Leu Thr Ile Ser Ser Val Glu
 65                  70                  75                  80

Ala Glu Asp Ala Ala Thr Tyr Tyr Cys Gln Gln Tyr Ser Gly Tyr Arg
                 85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Arg Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 6
<211> LENGTH: 462
<212> TYPE: PRT
<213> ORGANISM: Artificial Sequence
<220> FEATURE:
<223> OTHER INFORMATION: Description of Artificial Sequence:Amino acid
      sequence for heavy chain of recombinant antibody with C-terminal
      histidine tag sequence

<400> SEQUENCE: 6

Glu Val Gln Leu Gln Gln Ser Gly Pro Glu Leu Val Lys Pro Gly Ala
  1               5                  10                  15

Ser Val Met Ile Ser Cys Arg Thr Ser Ala Tyr Thr Phe Thr Glu Asn
             20                  25                  30

Thr Val His Trp Val Lys Gln Ser His Gly Glu Ser Leu Glu Trp Ile
             35                  40                  45

```
Gly Gly Ile Asn Pro Tyr Tyr Gly Gly Ser Ile Phe Ser Pro Lys Phe
    50                  55                  60

Lys Gly Lys Ala Thr Leu Thr Val Asp Lys Ser Ser Thr Ala Tyr
65              70                  75                  80

Met Glu Leu Arg Ser Leu Thr Ser Glu Asp Ser Ala Val Tyr Tyr Cys
                85                  90                  95

Ala Arg Arg Ala Gly Ala Tyr Tyr Phe Asp Tyr Trp Gly Gln Gly Thr
            100                 105                 110

Thr Leu Thr Val Ser Ser Ala Lys Thr Thr Pro Pro Ser Val Tyr Pro
        115                 120                 125

Leu Ala Pro Gly Cys Gly Asp Thr Thr Gly Ser Ser Val Thr Leu Gly
    130                 135                 140

Cys Leu Val Lys Gly Tyr Phe Pro Glu Ser Val Thr Val Thr Trp Asn
145                 150                 155                 160

Ser Gly Ser Leu Ser Ser Ser Val His Thr Phe Pro Ala Leu Leu Gln
                165                 170                 175

Ser Gly Leu Tyr Thr Met Ser Ser Ser Val Thr Val Pro Ser Ser Thr
            180                 185                 190

Trp Pro Ser Gln Thr Val Thr Cys Ser Val Ala His Pro Ala Ser Ser
            195                 200                 205

Thr Thr Val Asp Lys Lys Leu Glu Pro Ser Gly Pro Ile Ser Thr Ile
    210                 215                 220

Asn Pro Cys Pro Pro Cys Lys Glu Cys His Lys Cys Pro Ala Pro Asn
225                 230                 235                 240

Leu Glu Gly Gly Pro Ser Val Phe Ile Phe Pro Pro Asn Ile Lys Asp
                245                 250                 255

Val Leu Met Ile Ser Leu Thr Pro Lys Val Thr Cys Val Val Val Asp
            260                 265                 270

Val Ser Glu Asp Asp Pro Asp Val Gln Ile Ser Trp Phe Val Asn Asn
    275                 280                 285

Val Glu Val His Thr Ala Gln Thr Gln Thr His Arg Glu Asp Tyr Asn
290                 295                 300

Ser Thr Ile Arg Val Val Ser Thr Leu Pro Ile Gln His Gln Asp Trp
305                 310                 315                 320

Met Ser Gly Lys Glu Phe Lys Cys Lys Val Asn Asn Lys Asp Leu Pro
                325                 330                 335

Ser Pro Ile Glu Arg Thr Ile Ser Lys Ile Lys Gly Leu Val Arg Ala
            340                 345                 350

Pro Gln Val Tyr Ile Leu Pro Pro Pro Ala Glu Gln Leu Ser Arg Lys
        355                 360                 365

Asp Val Ser Leu Thr Cys Leu Val Val Gly Phe Asn Pro Gly Asp Ile
    370                 375                 380

Ser Val Glu Trp Thr Ser Asn Gly His Thr Glu Glu Asn Tyr Lys Asp
385                 390                 395                 400

Thr Ala Pro Val Leu Asp Ser Asp Gly Ser Tyr Phe Ile Tyr Ser Lys
                405                 410                 415

Leu Asn Met Lys Thr Ser Lys Trp Glu Lys Thr Asp Ser Phe Ser Cys
            420                 425                 430

Asn Val Arg His Glu Gly Leu Lys Asn Tyr Tyr Leu Lys Lys Thr Ile
        435                 440                 445

Ser Arg Ser Pro Gly Lys Gly Gly His His His His His His
450                 455                 460
```

<210> SEQ ID NO 7
<211> LENGTH: 80
<212> TYPE: DNA
<213> ORGANISM: Artificial Sequence
<220> FEATURE:
<223> OTHER INFORMATION: Description of Artificial Sequence:HC 5' coding
      strand primer RAPHC-5

<400> SEQUENCE: 7
gccaccatgg aatggagttg gatatttctc tttctcctgt caggaactgc aggtgtccac      60
tctgaggtcc agctgcarca                                                  80

<210> SEQ ID NO 8
<211> LENGTH: 80
<212> TYPE: DNA
<213> ORGANISM: Artificial Sequence
<220> FEATURE:
<223> OTHER INFORMATION: Description of Artificial Sequence: LC 5'-
      coding strand primer RAPLC-5.

<400> SEQUENCE: 8
gccaccatgg attttctggt gcagattttc agcttcttgc taatcagtgc ctcagttgca      60
atgtccagag gagaaaatgt                                                  80

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence:HC 3'
      non-coding strand primer

<400> SEQUENCE: 9
ctaagctcat ttacccggag accg                                             24

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence:LC 3'
      non-coding strand primer

<400> SEQUENCE: 10
ctcaggacct ttgtctctaa cactc                                            25

<210> SEQ ID NO 11
<211> LENGTH: 62
<212> TYPE: DNA
<213> ORGANISM: Artificial Sequence
<220> FEATURE:
<223> OTHER INFORMATION: Description of Artificial Sequence:HC His 5'
      coding strand primer

<400> SEQUENCE: 11
ctcccggtct ccgggtaaag gtggccatca ccaccatcac cattgagctt agaagggcaa      60
tt                                                                     62

<210> SEQ ID NO 12
<211> LENGTH: 62
<212> TYPE: DNA
<213> ORGANISM: Artificial Sequence
<220> FEATURE:
<223> OTHER INFORMATION: Description of Artificial Sequence:HC His 5'
      non-coding strand primer

```
<400> SEQUENCE: 12
aattgccctt ctaagctcaa tggtgatggt ggtgatggcc acctttaccc ggagaccggg         60
ag                                                                       62
```

RECOMBINANT MONOCLONAL ANTIBODY TO PHOSPHOTYROSINE-CONTAINING PROTEINS

FIELD OF THE INVENTION

The present invention relates to the field of recombinant monoclonal antibodies and their uses in clinical and scientific procedures, including diagnostic procedures, especially where such processes involve the detection of phosphotyrosine-containing proteins.

BACKGROUND OF THE INVENTION

Cellular growth, especially the uncontrolled growth seen in cancers, has, at least partly, been attributed to the functions of protein kinases that add phosphate to the hydroxyl group of tyrosine. In a similar way, oncogenic transformation of cells by entities such as Rous sarcoma virus and murine leukemia virus, leads to a significant increase, by at least an order of magnitude, in the level of phosphotyrosines seen in both virus-encoded proteins and proteins found in the transformed cells. Tyrosine kinases are believed intimately involved in such transformation processes.

Anti-phosphotyrosine monoclonal antibodies specific for proteins containing phosphotyrosine residues have proven valuable in studying such transformation processes, as well as in the detection of phosphotyrosine residues in proteins and detection of proteins containing such moieties. Thus, because oncogenes present in transforming organisms have been found to have natural counterparts, or homologs, within the untransformed cells, tyrosine-kinases have been implicated in normal growth control, possibly including during embryonic development or regeneration. Consequently, the availability of significant quantities of monoclonal antibodies with specificity directed toward such proteins can be of far reaching value, especially where methods are available for the production of such antibodies on a high scale. For example, monoclonal antibodies can facilitate the identification of cellular substrates for tyrosine kinases and make possible affinity purification of their substrates as well as being highly useful in screening for, and detecting, diseases.

Modern technology, such as that involving the use of hybridomas, has made available to researchers and clinicians alike sources of highly specific and potent monoclonal antibodies useful in general diagnostic and clinical procedures, such as where these antibodies are specific for phosphotyrosine-containing proteins and polypeptides. Among the more useful monoclonal antibodies are those derived from the 4G10 hybridoma cell line. The 4G10 monoclonal antibody is described further in Oda et al, *Blood*, Crkl is constitutively tyrosine phosphorylated in platelets from chronic myelogenous leukemia patients and inducibly phosphorylated in normal platelets stimulated by thrombopoietin, 88(11):4304–13 (Dec. 1, 1996). However, while such antibodies are useful, they are not easy to produce in pure form. For example, the 4G10 cell line is a low producer of the required antibodies and therefor it is difficult, as well as expensive, to procure such antibodies in sufficient quantity to support all the different uses to which they might be put. In addition, the quality of said antibodies from one lot to another may also be less that what is desired by most researchers and clinicians.

More specifically, the purified His tagged recombinant antibody is purer than what can be obtained from the hybridoma source. The hybridoma Protein A purified 4G10 has an as yet unidentified heavy chain doublet whereas the IMAC purified recombinant antibody of the present invention is highly pure with a single heavy chain band and light chain band. Furthermore, the phosphotyrosine binding properties of 4G10 are sensitive to acid exposure and elution from Protein A or G columns with the required low pH conditions leads to partial inactivation and thus a lower specific activity.

The present invention solves such problems by offering a recombinant monoclonal antibody comprising utility and specificity the same or similar to that derived from the 4G10 hybridoma cell line but showing much greater purity with concomitant high specific activity and consistency of performance. Especially useful is the histidine-tagged form of the immunoglobulin of the present invention. The His tag allows for IMAC (immobilized metal affinity chromatography) purification under neutral pH conditions so that the recombinant antibody is never exposed to low pH conditions. Greater purity is, of course, highly useful in clinical applications.

The His tag is also useful in that it facilitates attachment of the recombinant antibody or immunoglobulin in an orientated fashion to Nickel matrices for solid phase applications. Thus, the His tagged recombinant form is particularly useful. The methods disclosed herein thus afford a purer and more uniform product with generally higher specific activity.

BRIEF SUMMARY OF THE INVENTION

The present invention relates to a recombinant monoclonal antibody having specificity directed to proteins and polypeptides comprising phosphotyrosine moieties.

It is therefore an object of the present invention to provide for a recombinant monoclonal antibody having specificity for phosphotyrosine-containing proteins and polypeptides.

It is a further object of the present invention to provide polynucleotides, such as cDNAs, whose nucleotide sequences code for the heavy and light chains of the aforementioned recombinant antibodies and immunoglobulins.

It is a still further object of the present invention to provide recombinant antibodies specific for phosphotyrosine-containing proteins and polypeptides wherein said antibodies are tagged with sequences of amino acids, and other tags, making them easily isolatable as well as affording versatility in using said antibodies for research, diagnostic and clinical purposes.

It is another object of the present invention to provide a method of using the recombinant antibodies disclosed herein for research, diagnostic and clinical uses.

BRIEF DESCRIPTION OF THE DRAWINGS

FIG. 3 shows an immunoprecipitation immunoblot of EGF stimulated A431 cell extracts. 500 µg of cell extract was immunoprecipitated (IP) with 4 µg of recombinant or native 4G10 antibody purified from CHO cells and probed with recombinant or native 4G10 at a concentration of 2 µg/ml. Lane 1, IP-antibody=r4G10 (recombinant 4G10), no primary antibody; Lane 2, IP-antibody=native 4G11, no primary antibody; Lane 3, IP-antibody=r4G10, primary antibody=r4G10; Lane 4, IP-antibody=native 4G10, primary antibody=r4G10; Lane 5, IP-antibody=r4G10, primary antibody=native 4G10; Lane 6, IP-antibody=native 4G10, primary antibody=native 4G10. Molecular weight markers in kilodaltons are indicated at the left.

DETAILED SUMMARY OF THE INVENTION

Figure 1:
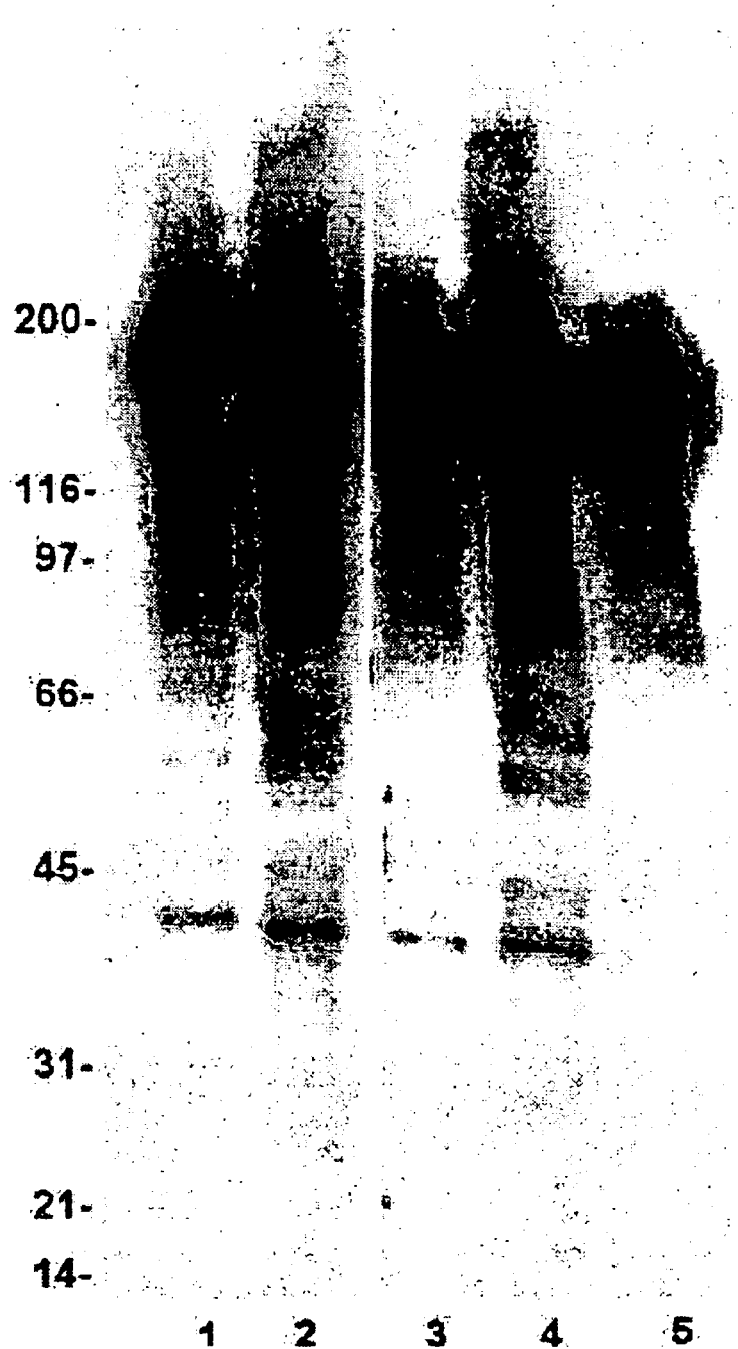
FIG. 1 shows an immunoblot of EGF (epidermal growth factor) stimulated A431 cell extracts probed with conditioned media from COS cells transfected with 4G10 hybridoma light chain and heavy chain cDNAs. Lane 1, HC clone-42 and LC clone-14; Lane 2, HC clone-42 and LC clone-11; Lane 3, HC clone-44 and LC clone-14; Lane 4, HC clone-44 and LC clone-11; Lane 5, native 4G10 at 1 µg/ml. Molecular weight markers in kilodaltons are indicated at the left.

With the advent of methods of molecular biology and recombinant technology, it is now possible to produce antibody molecules by recombinant means and thereby generate gene sequences that code for specific amino acid sequences found in the polypeptide structure of the antibodies. Such antibodies can be produced by either cloning the gene sequences encoding the polypeptide chains of said antibodies or by direct synthesis of said polypeptide chains, with in vitro assembly of the synthesized chains to form active tetrameric ($H_2L_2$) structures with affinity for specific epitopes and antigenic determinants. This has permitted the ready production of antibodies having sequences characteristic of neutralizing antibodies from different species and sources.

Regardless of the source of the antibodies, or how they are recombinantly constructed, or how they are synthesized, in vitro or in vivo, using transgenic animals, such as cows, goats and sheep, using large cell cultures of laboratory or commercial size, in bioreactors or by direct chemical synthesis employing no living organisms at any stage of the process, all antibodies have a similar overall 3 dimensional structure. This structure is often given as $H_2L_2$ and refers to the fact that antibodies commonly comprise 2 light (L) amino acid chains and 2 heavy (H) amino acid chains. Both chains have regions capable of interacting with a structurally complementary antigenic target. The regions interacting with the target are referred to as "variable" or "V" regions and are characterized by differences in amino acid sequence from antibodies of different antigenic specificity.

The variable regions of either H or L chains contains the amino acid sequences capable of specifically binding to antigenic targets. Within these sequences are smaller sequences dubbed "hypervariable" because of their extreme variability between antibodies of differing specificity. Such hypervariable regions are also referred to as"complementarity determining regions" or "CDR" regions. These CDR regions account for the basic specificity of the antibody for a particular antigenic determinant structure.

The CDRs represent non-contiguous stretches of amino acids within the variable regions but, regardless of species, the positional locations of these critical amino acid (sequences within the variable heavy and light chain regions have been found to have similar locations within the amino acid sequences of the variable chains. The variable heavy and light chains of all antibodies each have 3 CDR regions, each non-contiguous with the others (termed L1, L2, L3, H1, H2, H3) for the respective light (L) and heavy (H) chains. The accepted CDR regions have been described by Kabat et al, *J. Biol. Chem.* 252:6609–6616 (1977).

In all mammalian species, antibody polypeptides contain constant (i.e., highly conserved) and variable regions, and, within the latter, there are the CDRs and the so-called "framework regions" made up of amino acid sequences within the variable region of the heavy or light chain but outside the CDRs.

In accordance with the foregoing, the present invention is directed generally to a recombinant monoclonal antibody having specificity directed to proteins and polypeptides comprising phosphotyrosine moieties.

The present invention further relates to a polypeptide which has the deduced amino acid sequence (SEQ ID NO: 4, 5 or 6), as well as immunologically active fragments, analogs and derivatives of such polypeptide.

The terms "fragment," "derivative" and "analog" when referring to a polypeptide (such as SEQ ID NO: 4, 5 or 6), means a fragment, derivative or analog of the polypeptide that retains essentially the same biological function or activity as such polypeptide. Thus, an analog includes a proprotein which can be activated by cleavage of the proprotein portion to produce an active mature polypeptide. Such fragments, derivatives and analogs must have sufficient similarity to the polypeptide of SEQ ID NO: 4, 5 or 6 so that the immunological activity and/specificity of the native polypeptide is retained. In accordance with the present invention, when composing antibodies, such a fragment would include Fab and F(ab')$_2$ fragments but the invention is in no way limited only to such fragments.

The polypeptide of the present invention may be a recombinant polypeptide, a natural polypeptide or, in general, a synthetic polypeptide, meaning a polypeptide other than one occurring naturally, preferably a recombinant polypeptide having the immunological specificity and/or activity disclosed herein and including immunologically active fragments thereof. The antibodies formed of the polypeptides of the present invention may likewise be dimeric in nature, consisting of only one heavy and one light chain, or may be chimeric or humanized or other form of recombinant antibody.

The immunoglobulins of the present invention include those with amino acid sequences substantially identical to the sequences of SEQ ID NO: 4, 5 or 6. As used herein, the term "substantially identical" includes sequences at least 98% identical to the sequences disclosed herein or sequences wherein (i) one or more of the amino acid residues are substituted with a conserved or non-conserved amino acid residue (preferably a conserved amino acid residue) which is of the same chemical character as the amino acid being substituted for, such as where a hydrophobic residue is replaced by another hydrophobic residue, or where an acidic residue is replaced by another acidic residue, or where a basic residue is replaced by another basic residue, or where a polar residue is replaced by another polar residue, especially where the respective amino acids are of similar size. Such amino acids may also be replaced by amino acids of similar size and chemical character but which are not amino acids normally coded for by the genetic code or where one or more of the amino acid residues includes a specialized substituent group. The purified, or highly pure, immunoglobulins of the present invention may also be fused with another compound, such as a compound to increase the half-life of the polypeptide (for example, polyethylene glycol), or where the additional amino acids are fused to the mature polypeptide, such as a leader or secretory sequence or a sequence which is employed for purification of the mature polypeptide or a proprotein sequence. Such analogs are deemed to be within the scope of those skilled in the art from the teachings herein.

The immunoglobulins of the present invention are preferably provided in an isolated form, and preferably are purified to homogeneity.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

As used herein, the terms "portion," "segment," and "fragment," when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide.

Figure 5:
FIG. 5 shows that His-tagged recombinant 4G 10 is purer than native (commercially available) 4G10 as determined by SDS-PAGE. Lane 1, 6 micrograms of His-tagged r4G10 (r=recombinant); Lane 2, Molecular weight marker; Lane 3, 6 micrograms of native 4G10. Molecular weight markers in kilodaltons are indicated at the left.

In accordance with the foregoing, the present invention relates to a purified or highly pure immunoglobulin having the same specificity as 4G10 monoclonal antibody (available commercially from Upstate Biotechnology Inc., Lake Placid, N.Y.). This purified immunoglobulin, which term includes antibodies, such as monoclonal antibodies, regardless of how prepared, including by direct chemical synthesis, comprises two light chain components and two heavy chain components wherein said heavy chain components exhibit a single band on gel electrophoresis. The commercially available form heretofore available exhibits a heavy chain doublet and thus shows lower specific activity and reproducibility than the purified immunoglobulin of the present invention (comparison shown in FIG. 5). As used herein, the terms "purified" and "highly pure" or "highly purified" refer to immunoglobulins having the same or substantially the same specificity as the 4G10 antibody but showing a gel pattern similar to that exhibited by the immunoglobulins, or antibodies, of the present invention, especially in that they exhibit only a single heavy chain band, as shown in FIG. 5, and not the doublet found for previously available 4G 10 monoclonal antibody.

In one embodiment, highly pure or purified immunoglobulin of the present invention comprises a histidine tag region. Again, this embodiment commonly comprises two light chain components and two heavy chain components wherein said heavy chain components exhibit a single band on gel electrophoresis. In a specific embodiment, said histidine tag is part of the heavy chain component of said antibody or immunoglobulin.

In specific embodiments of the present invention, the isolated polypeptides disclosed herein may comprise tags or other markers, including specific sequences of amino acids, especially where said sequence is composed of histidine residues, for example, a run of 6 histidine residues (such as with the polypeptide of SEQ ID NO: 6), and any additional alterations in said polypeptide necessary for attaching said marker, such as said histidine sequence, to the polypeptides of the invention. Such sequences are commonly, but need not necessarily be, attached to the COOH-terminal of the polypeptide sequences disclosed herein. In addition, where said polypeptide is encoded by a polynucleotide of the present invention, a nucleotide sequence encoding said marker sequence, such as a nucleotide sequence encoding a histidine tag sequence, may be part of the polynucleotide sequences of the invention.

In specific embodiments of the present invention, the polypeptide having SEQ ID NO: 6 is an example of an amino acid sequence representing a heavy chain polypeptide according to the present invention wherein the C-terminal of said chain has attached thereto a hexapeptide sequence composed of histidine residues. Corresponding to this is the polynucleotide having the nucleotide sequence of SEQ ID NO: 3, which encodes the polypeptide of SEQ ID NO: 6, and comprises at its 3'-end a nucleotide sequence coding for said histidine tag sequence. Other markers, tags, and amino acid sequences, configurations, and the like, useful for tagging the polypeptide of interest will no doubt occur to those of skill in the art once possessed of the disclosure of the present invention.

In a specific embodiment, the highly pure or purified immunoglobulin of the present invention comprises a heavy chain component whose amino acid sequence is substantially the same as the sequence of SEQ ID NO: 4. In another specific embodiment, the purified or highly pure immunoglobulin of the present invention comprises a light chain component whose amino acid sequence is substantially the same as the sequence of SEQ ID NO: 5. In a preferred embodiment, the highly pure or purified immunoglobulin of the present invention comprises a heavy chain component whose amino acid sequence is substantially the same as the sequence of SEQ ID NO: 4 and a light chain component whose amino acid sequence is substantially the same as the sequence of SEQ ID NO: 5.

In other specific embodiments, the purified or highly pure immunoglobulin of the present invention comprises a heavy chain component whose amino acid sequence is substantially the same as the sequence of SEQ ID NO: 6. In a preferred embodiment, said sequence is that of SEQ ID NO: 6.

The present invention also relates to isolated polynucleotide sequences encoding the polypeptides of which the antibodies of the present invention are comprised.

Thus, the present invention relates to an isolated polynucleotide encoding a polypeptide as disclosed herein including the complements of such polynucleotides. The isolated polynucleotides of the present invention include cDNAs. In specific embodiments, such polynucleotides include the polynucleotides having the sequences of SEQ ID NOs: 1, 2, and 3 and sequences sufficiently identical thereto so as to encode a protein substantially identical to the polypeptides of the immunoglobulins of the present invention. Such variability may also be due to the degeneracy of the genetic code.

In another aspect, the present invention also relates to a method of producing a highly purified immunoglobulin comprising the steps of:

(a) inserting a histidine tag sequence at the C-terminal end of the heavy chain component of an immunoglobulin to be purified to produce a histidine tagged immunoglobulin;

(b) purifying said histidine tagged heavy chain polypeptide by immobilized metal affinity chromatography under neutral conditions and specifically preventing exposure of the immunoglobulin to acidic pH;

(c) recovering the purified histidine tagged highly purified immunoglobulin.

The methods of the invention are further described in more detail in the methods and examples below. The methods of the present invention also contemplate purification schemes wherein the heavy chain component is produced by expression of a polynucleotide encoding said histidine tagged heavy chain component, such as a cDNA encoding such a tagged chain. One example of such a cDNA is the polynucleotide sequence of SEQ ID NO: 3. A novel aspect of the methods of purification disclosed herein is the use of neutral, or relatively neutral, pH conditions during the immobilized metal affinity chromatography (IMAC) step in that, avoidance of any acidic pH exposure preserves the immunoglobulin, thereby affording highly pure or purified immunoglobulins. Such methodology may be readily applied to the production of other highly purified immunoglobulins (i.e., antibodies), even those with specificities different from those of the present invention. In keeping with the disclosure herein, to be avoided are pH values of 6.5 and below, preferably 6.0 and below, most preferably 5.5 and below, especially 5.0 and below and most especially 4.0 and below.

In another aspect, therefore, the present invention is directed to an immunoglobulin produced by the methods of production and purification disclosed according to the present invention (as detailed above and in the examples).

In accordance with the present invention, the term "percent identity" or "percent identical," when referring to a sequence, means that a sequence is compared to a claimed or described sequence after alignment of the sequence to be compared (the "Compared Sequence") with the described or claimed sequence (the "Reference Sequence"). The Percent Identity is then determined according to the following formula:

Percent Identity=100 [1−(C/R)]

wherein C is the number of differences between the Reference Sequence and the Compared Sequence over the length of alignment between the Reference Sequence and the Compared Sequence wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference; and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the hereinabove calculated Percent Identity is less than the specified Percent Identity. The alignment boundary is the length of the Reference Sequence or claimed sequence that is being compared.

The recombinant polynucleotides and polypeptides disclosed herein may be prepared by direct chemical synthesis thereof in light of the sequences disclosed or may be prepared by recombinant means well known in the molecular biological arts. Consequently, as used herein and except as noted otherwise, all terms are defined as given below.

In accordance with the present invention, the term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, using a cloning vector. Such segments are provided in the form of an open reading frame uninterrupted by internal nontranslated sequences, or introns, which are typically present in eukaryotic genes. Sequences of non-translated DNA may be present downstream from the open reading frame, where the same do not interfere with manipulation or expression of the coding regions.

The nucleic acids and polypeptide expression products disclosed according to the present invention, as well as expression vectors containing such nucleic acids and/or such polypeptides, may be in "enriched form." As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in enriched or isolated form.

"Isolated" in the context of the present invention with respect to polypeptides (or polynucleotides) means that the material is removed from its original environment (e.g., the natural environment if it is naturally occurring). For example, a naturally-occurring polynucleotide or polypeptide present in a living organism is not isolated, but the same polynucleotide or polypeptide, separated from some or all of the co-existing materials in the natural system, is isolated. Such polynucleotides could be part of a vector and/or such polynucleotides or polypeptides could be part of a composition, and still be isolated in that such vector or composition is not part of its natural environment. The polypeptides and polynucleotides of the present invention are preferably provided in an isolated form, and preferably are purified to homogeneity.

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, claimed polypeptide which has a purity of preferably 0.001%, or at least 0.01% or 0.1%; and even desirably 1% by weight or greater is expressly contemplated.

The term "coding region" refers to that portion of a gene which either naturally or normally codes for the expression product of that gene in its natural genomic environment, i.e., the region coding in vivo for the native expression product of the gene. The coding region can be from a normal, mutated or altered gene, or can even be from a DNA sequence, or gene, wholly synthesized in the laboratory using methods well known to those of skill in the art of DNA synthesis.

In accordance with the present invention, the term "nucleotide sequence" refers to a heteropolymer of deoxyribonucleotides. Generally, DNA segments encoding the proteins provided by this invention are assembled from cDNA fragments and short oligonucleotide linkers, or from a series of oligonucleotides, to provide a synthetic gene which is capable of being expressed in a recombinant transcriptional unit comprising regulatory elements derived from a microbial or viral operon.

The term "expression product" means that polypeptide or protein that is the natural translation product of the gene and any nucleic acid sequence coding equivalents resulting from genetic code degeneracy and thus coding for the same amino acid(s).

The term "fragment," when referring to a coding sequence, means a portion of DNA comprising less than the complete coding region whose expression product retains essentially the same biological function or activity as the expression product of the complete coding region.

The term "primer" means a short nucleic acid sequence that is paired with one strand of DNA and provides a free 3'OH end at which a DNA polymerase starts synthesis of a deoxyribonucleotide chain.

The term "promoter" means a region of DNA involved in binding of RNA polymerase to initiate transcription.

The term "open reading frame (ORF)" means a series of triplets coding for amino acids without any termination codons and is a sequence (potentially) translatable into protein.

As used herein, reference to a DNA sequence includes both single stranded and double stranded DNA. Thus, the specific sequence, unless the context indicates otherwise, refers to the single strand DNA of such sequence, the duplex of such sequence with its complement (double stranded DNA) and the complement of such sequence.

Methods useful in the recombinant procedures disclosed herein are described in such compendiums as Sambrook, et al., Molecular Cloning: A Laboratory Manual, Second Edition, Cold Spring Harbor, N.Y., (1989), Wu et al, *Methods in Gene Biotechnology* (CRC Press, New York, N.Y., 1997), and *Recombinant Gene Expression Protocols*, in *Methods in Molecular Biology*, Vol. 62, (Tuan, ed., Humana Press, Totowa, N.J., 1997), the disclosures of which are hereby incorporated by reference in their entirety.

The present invention further relates to a functional, antigen-specific immunoglobulin molecule, which includes dimeric or tetrameric structures comprised of either a light and heavy chain, or two light plus two heavy chains. The highly pure or purified immunoglobulins of the present invention show a single band for the heavy chain on a gel as described in FIG. 5 and as distinguished from the presently available 4G10 monoclonal antibody produced from 4G10 hybridoma cells. Of course, substitution of amino acids of similar size and chemical properties will alter the sequence of the light and heavy chain polypeptides making up the immunoglobulins of the present invention but will not produce distinctly separate bands on gels run as disclosed herein and thus will still differ from the presently known 4G10 monoclonal antibody.

In other embodiments, the present invention further relates to purified or highly pure immunoglobulins or monoclonal antibodies exhibiting the same or similar antigenic specificity as 4G10 monoclonal antibody and wherein said antibody demonstrates positive reactivity with phosphotyrosine containing proteins. In a one embodiment, such purified or highly pure immunoglobulins demonstrate:

(a) positive reactivity with phosphotyrosine containing proteins; and (b) lack of reactivity with phosphoserine or phosophothreonine proteins.

In other embodiments of the present invention, such immunoglobulins exhibit positive reactivity with phosphotyrosine-containing proteins from animal cells, especially wherein the antibody demonstrates positive reactivity with phosphotyrosine-containing proteins from human cells.

The present invention also relates to vectors comprising a polynucleotide as disclosed herein and to recombinant or genetically engineered cells capable of expressing said polynucleotides after transfected or transformed with said vectors, most especially where the expressed polynucleotides result in polypeptides that are secreted from the cells.

In one embodiment, a cell is transfected with one or more of the vectors disclosed herein to form a recombinant cell that expresses the polynucleotides contained in said vector to form at least two different polypeptides wherein each polypeptide represents either the heavy or the light chain of an antibody according to the present invention. In such an embodiment, a recombinant cell expresses a polynucleotide encoding a light chain and another polynucleotide encoding a heavy chain for an antibody according to the invention. Such antibodies are then assembled within the cell and secreted in a form capable of binding to an antigen.

Methods of genetically engineering such cells are well known in the literature [see, for example, the methods disclosed in Morrison et al, U.S. Pat. No. 5,807,715, the disclosure of which is hereby incorporated by reference in its entirety; see also Ochi et al, *PNAS*, 80, 6351–55 (1983); Johnson, U.S. Pat. No. 5,824,307]. Cells useful for such methods include most lymphoid cells, such as myelomas, hybridomas, and plasmacytomas, as well as cell lines such as CHO cells.

Recombinant cells of the present invention include cells producing antibodies that demonstrate positive reactivity with phosphotyrosine-containing proteins from human cells.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli*. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli, Streptomyces, Salmonella typhimurium*; fungal cells, such as yeast; insect cells such as *Drosophila* S2 and *Spodoptera* Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pBluescript SK, pBSKS, pNH8A, pNH16a, pNH18A, pNH46A (Stratagene); pTRC99a, pKK223-3, pKK233-3, pDR540, pRIT5 (Pharmacia); Eukaryotic: pWLNE0, pSV2CAT, p0G44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* Trp1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptides, or antibodies, of the present invention are recovered and purified from recombinant cells as disclosed herein. Protein refolding steps can be used, as necessary, in completing configuration of the mature protein. Finally, high performance liquid chromatography (HPLC) can be employed for final purification steps as well as IMAC (immobilized metal affinity chromatography).

A polypeptide of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The present invention also relates to an immunosorbent material comprising the purified or highly pure immunoglobulins as disclosed herein and a microporous polymeric substrate. In one embodiment, such microporous polymeric substrate comprises a plurality of beads, said beads having diameters on the order of no larger than about 100 microns, preferably no larger than about 10 microns, most preferably about 5 microns with an especially preferred embodiment using beads 5 microns (or micrometers) in diameter. In a specific embodiment of the present invention, the substrate is polymerized agarose.

In another embodiment using such microporous polymeric substrate, such as the aforementioned plurality of beads, such substrate comprises one or more metal ions, or other metal ligands, which metal ligands bind the histidine tagged portion of a histidine tagged antibody. Such an antibody may be the histidine tagged antibody of the invention. As described herein, such antibodies are commonly highly pure or purified (meaning an antibody with the same or similar degree of purity of that antibody disclosed herein as determined, for example, by the gel pattern shown for the purified or highly pure 4G 10-specific antibody of the invention). Such a ligand-attached substrate (serving as a metal affinity matrix, i.e., a surface comprising a metal ligand capable of binding to a histidine tagged protein, such as an antibody, especially a histidine tagged 4G10-specific antibody of the present invention) is useful for attaching to the histidine-tagged portion of the antibodies of the present invention in methods other than just for purification. Thus, such methods are easily adapted to assay and screening processes and are not limited to purification schemes although other and different uses will no doubt suggest themselves to those skilled in the art yet such uses are still within the methods disclosed according to the present invention.

In accordance with the foregoing, the present invention further relates to a method of detecting the presence of phosphotryosine-containing proteins in a sample comprising the steps of contacting the sample with an antibody of the present invention and testing for reactivity wherein a positive reaction demonstrates the presence of a phosphotyrosine-containing protein or polypeptide in said sample.

Specific embodiments of the present invention comprise methods wherein the step of testing the sample further comprises contacting the sample with an immunosorbent material which includes the monoclonal antibodies. In preferred embodiments, the step of testing further comprises testing by a method selected from the group consisting of immunofluorescence, radioimmunoassay, immunoprecipitation, complement fixation, competitive reaction, Western blotting, immunohistochemistry, flow cytometry, and enzyme-linked immunosorbent assay (ELISA).

The monoclonal antibodies of the present invention serve as a high titer, reproducible, biological reagent useful in biological/medical research for isolating and identifying phosphotyrosine-containing proteins, with potential uses in diagnosis of a variety of diseases, including certain cancers. The antibodies, which have demonstrated affinity for a variety of molecules containing phosphotyrosine residues, were prepared recombinantly from corresponding cDNAs and have properties indistinguishable from those of commercially available antibodies produced by the 4G10 hybridoma cell line.

Among the utilities for the antibodies disclosed according to the present invention include applications to identify cellular substrates for tyrosine kinases and make possible the affinity purification of a wide variety of phosphotyrosine-proteins, including clinical and diagnostic assays for such things as platelet-derived growth factors (PDGF—and its cellular receptor), TGF (tumor growth factor) and determining the tyrosine phosphorylation status of one or multiple proteins in a given cell or tissue sample.

In one non-limiting example of such utility, a cell or tissue sample can be reacted with the monoclonal antibodies of the present invention and the immune complex of monoclonal antibody bound to proteins containing phosphotyrosines collected. Such an immunoprecipitation or immunoaffinity purification complex can be resolved and reacted by a variety of procedures (e.g. Western blotting, ELISA) with antibodies to the various known proteins to identify the phosphotyrosine proteins in the given sample. This analysis can be extended to the discovery of novel phosphotyrosine proteins by scaling up the immunoprecipitation or immunoaffinity purification and purifying the phosphotyrosine proteins and subjecting them to analytical procedures such as protein sequencing by Edman degradation or mass spectrometry. A further example of the aforementioned embodiment involves the immunoprecipitation or immunoaffinity purification of a known protein or proteins and reacting the resulting complex with the monoclonal antibodies of the present invention for determining phosphotyrosine status.

In a simple TGF assay method, a biological fluid, such as urine or blood serum, or other potential source of TGF from a patient can be reacted with a preparation of EGF receptors, for example, cell membranes from A431, a human epidermal carcinoma cell line with numerous EGF receptors per cell. Adenosine triphosphate (labeled in the .gamma.-phosphate with radioactive $^{32}$p or a thio analog labeled with $^{35}$S) is added as a source of phosphate. In the presence of TGF, the EGF receptor will incorporate labeled phosphate into its tyrosine residues. The reaction may then be terminated and the receptors extracted from the membrane. The receptors are then bound to monoclonal antibodies of the present invention (for example, using beads coated with the antibodies) and the radioactivity counted to provide a measure of the growth factor present in the sample. Assays for PDGF would follow a similar procedure employing a PDGF-sensitive receptor. Other assays may employ nerve growth factor receptors, insulin receptors, insulin-like growth factor receptors, sarcoma growth factor receptors and the like. Various modifications to these methods as well as other assay techniques employing our antibodies may be devised by those skilled in the art without departing from the spirit or scope of invention.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

The present invention will now be further described by way of the following non-limiting examples. In applying the disclosure of these examples, it should be kept clearly in mind that other and different embodiments of the methods disclosed according to the present invention will no doubt suggest themselves to those of skill in the relevant art.

EXAMPLE

Abbreviations: IP, immunoprecipitation; HC, heavy chain; LC, light chain; IgG, immunoglobulin; Mab, monoclonal antibody; ELISA, enzyme-linked immunosorbent assay; IMAC, Immobilized Metal Affinity Chromatography; SDS-PAGE, sodium dodecyl sulfate-polyacrylamide gel electrophoresis; HRP, horseradish peroxidase; ECL, enhanced chemiluminescence; PBS, phosphate buffered saline; nt, nucleotide; EGF, epidermal growth factor; EGFr epidermal growth factor receptor; CHO, Chinese Hamster Ovary;

The definitions of nomenclature and descriptions of general laboratory procedures used in this application can be found in Ausubel, F. M. et al., Current Protocols In Molecular Biology. Wiley Interscience, New York, N.Y. 1999. All kits and enzymes were used according to the manufacture's instructions.

Preparation of Cell Lysates

Adherent human A431 cells were twice washed with cold PBS and subsequently lysed with ice-cold modified RIPA buffer (50 mM Tris-HCl, pH 7.4; 1% NP-40; 0.25% Na-deoxycholate; 150 mM NaCl; 1 mM EDTA; 1 mM PMSF; 1 microgram/ml each Aprotinin, leupeptin, pepstatin; 1 mM $Na_3VO_4$;1 mM NaF; 1 ml per 10' cells/100 mm dish) by scraping cells off the dish with a plastic cell scraper. The cell suspension was transferred into a centrifuge tube and gently rocked at 4° C. for 15 minutes to lyse the cells. Lysates are centrifuged at 14,000×g for 15 minutes and the supernatant immediately transferred to a fresh tube. Protein concentration was determined with a Coomassie-based reagent (Coomassie® Plus Protein Assay Reagent, Pierce, Rockland, Ill.).

Immunoblotting (Western Blotting)

Twenty µg of cell lysates per individual lane were subjected to SDS-PAGE and proteins transferred to a nitrocellulose membrane. The nitrocellulose membrane is washed twice with distilled $H_2O$ and stained with Ponceau Red solution for 5 minutes to visualize protein bands. The molecular weight markers are marked with a ball point pen and the membrane blocked in freshly prepared PBS containing 3% nonfat dry milk for 20 minutes at room temperature with constant agitation. Primary antibody (native or recombinant 4G10) is diluted in PBS/3% nonfat dry milk and incubated with the membrane for 1 to 2 hours at room temperature or overnight at 4° C. The nitrocellulose membrane is washed five times for 3 to 5 minutes each with PBS containing 0.05% Tween 20 before incubation with the secondary antibody (goat-anti-mouse HRP conjugate) for 1 hour. The membrane is washed five times again before final detection of proteins with an ECL HRP substrate.

Mouse IgG ELISA.

To measure levels of recombinant antibody in conditioned media, a mouse IgG ELISA was developed using precoated 96 well protein G strip plates (Pierce, Rockland, Ill.). Standards or samples are added in a 100 µl volume to wells and incubated at 37° C. for 1 hour and then washed with PBS prior to adding PBS 3% non-fat milk for 30 min at 37° C. The plates are washed again and 100 µl of a anti-mouse HRP secondary antibody is added for 1 hour at 37° C. Wells are then washed 3× in PBS and developed with TMB substrate solution (Pierce, Rockland, Ill.), stopped with 50 µl of 2 N $H_2SO_4$, and absorbance at 450 nm determined.

Immun Precipitation.

A Protein A agarose bead slurry is washed twice with PBS and restored to a 50% slurry with PBS. The cell lysate is precleared by adding 100 microliters of the protein A agarose slurry per 1 ml of cell lysate and incubating at 4° C. for 10 minutes on a orbital shaker. The protein A beads are removed by centrifugation at 14,000×g at 4° C. for 10 minutes and supernatant transferred to a fresh centrifuge tube. The cell lysate is diluted with PBS to approximately 1 mg/ml total cell protein before addition of the immunoprecipitating antibody (IP-antibody) in a total volume of 500 microliters. The cell lysate/antibody mixture is incubated for 2 hours or overnight at 4° C. on an orbital shaker. The immuno-complex is captured by adding 100 microliters of the protein A agarose slurry and incubated for either 1 hour or overnight at 4° C. on an orbital shaker. The protein A bead-bound immuno-complex is collected by centrifugation for 5 seconds at 14,000 rpm and the supernatant discarded. The beads are washed 3 times with 800 microliters ice-cold modified RIPA buffer and then resuspended in 60 microliters of SDS-PAGE reducing buffer and boiled for 5 minutes to dissociate the immunocomplexes from the beads. The beads are collected by centrifugation and SDS-PAGE is performed with the supernatant fraction.

Cloning, Expression and Purification of the Recombinant 4G10 Monoclonal Antibody.

In order to clone the antibody heavy chain (HC) and light chain (LC) cDNAs from the 4G10 hybridoma cell line, two 5' oligonucleotide primers were designed based on the N-terminal amino acid sequencing of the LC and HC purified peptides. The HC 5' coding strand primer RAPHC-5

5'-GCC ACC ATG GAA TGG AGT TGG ATA TTT CTC TTT CTC CTG TCA GGA ACT GCA GGT GTC CAC TCT GAG GTC CAG CTG CAR CA (SEQ ID NO: 7)

consisted of 63 base oligonucleotide encoding the N-terminal leader secretion signal sequence with a Kozak translation initiation site fused to the first 17 nt (nucleotide) encoding the mature processed N-terminal HC. The LC 5' coding strand primer RAPLC-5

5'-GCC ACC ATG GAT TTT CTG GTG CAG ATT TTC AGC TTC TTG CTA ATC AGT GCC TCA GTT GCA ATG TCC AGA GGA GAA AAT GT (SEQ ID NO: 8)

consisted of A 63 base oligonucleotide encoding the N-terminal leader secretion signal sequence with a Kozak translation initiation site fused to the first 17 nucleotides encoding the mature processed N-terminal LC.

Design of the HC 3' non-coding strand primer

5'-CTA AGC TCA TTT ACC CGG AGA CCG (SEQ ID NO: 9)

for amplification of the C-terminal encoding portion of the HC cDNA was based on prior knowledge that the 4G10 monoclonal antibody HC constant region was of the class γ2b. Design of the LC 3' non-coding strand primer

5'-CTC AGG ACC TTT GTC TCT AAC ACT C(SEQ ID NO: 10)

for amplification of the C-terminal encoding portion of the LC cDNA was based on prior knowledge that the 4G10 monoclonal antibody LC constant region was of the class kappa. Oligonucleotides were synthesized by IDT (Integrated DNA Technologies Inc., Coralville, Iowa) using standard DNA synthesis chemistries.

Total RNA was purified from PBS washed snap-frozen 4G10 hybridoma cell pellets (approximately $1 \times 10^7$ cells per sample) using RNAzol™B (Tel-Test Inc, Friendswood, Tex.). Purified total RNA was ethanol precipitated and quantified by absorbance at 260 nm. First strand cDNA was synthesized by reverse transcribing 2 μg of total RNA with oligo(dT) using the SuperScript™ system (Gibco BRL, Gaithersburg, Md.). The Expand™ High Fidelity PCR system (Boehringer Mannheim, Indianapolis, Ind.) was used for polymerase chain reaction (PCR) amplification of 1 μl of newly made first strand cDNA. PCR amplification conditions were as follows: after heating PCR components to 94° C., 1 μl of cDNA was added to each tube. Subsequent cycling conditions were 94° C. for 15 s, 50° C. for 1 min, and 72° C. for 1 min for 17 cycles for LC amplification and 21 cycles for HC amplification with a final extension of 72° C. for 10 min. LC and HC PCR products were purified from ethidium bromide stained agarose gels and cloned into the eukaryotic expression vector pcDNA3.1 (Invitrogen Corporation, San Diego, Calif.) and transformed into E. coli competent cells according to the manufacture's instructions. For each LC or HC plasmid construct, at least 4 individual E. coli plasmid clones were sequenced by standard automated DNA sequencing methods and the nucleotide consensus sequence minus the N-terminal leader secretion signal sequence are described in SEQ ID NO: 1 and SEQ ID NO: 2. The deduced polypeptide sequence translated from SEQ ID NO: 1 and SEQ ID NO: 2 are designated SEQ ID NO: 3 and SEQ ID NO: 4.

A hexa-histidine sequence was added to the C-terminus of the HC clone pHC-42 by site directed mutagenesis using a commercial kit (QuickChange™, Stratagene, La Jolla, Calif.) according to the manufacture's instructions. The following complementary oligonucleotides were used for introducing the hexa-histidine sequence: coding strand primer HC-His 5'

5'-CTC CCG GTC TCC GGG TAA AGG TGG CCA TCA CCA CCA TCA CCA TTG AGC TTA GAA GGG CAA TT (SEQ ID NO: 11)

and non-coding strand primer HC-His 5'

5'-AAT TGC CCT TCT AAG CTC AAT GGT GAT GGT GGT GAT GGC CAC CTT TAC CCG GAG ACC GGG AG-3' (SEQ ID NO: 12)

Successful introduction of the hexa-histidine encoding region was confirmed by DNA sequencing and corresponds to the polynucleotide sequence of SEQ ID NO: 3 which encodes the polypeptide of SEQ ID NO: 6.

Figure 2:
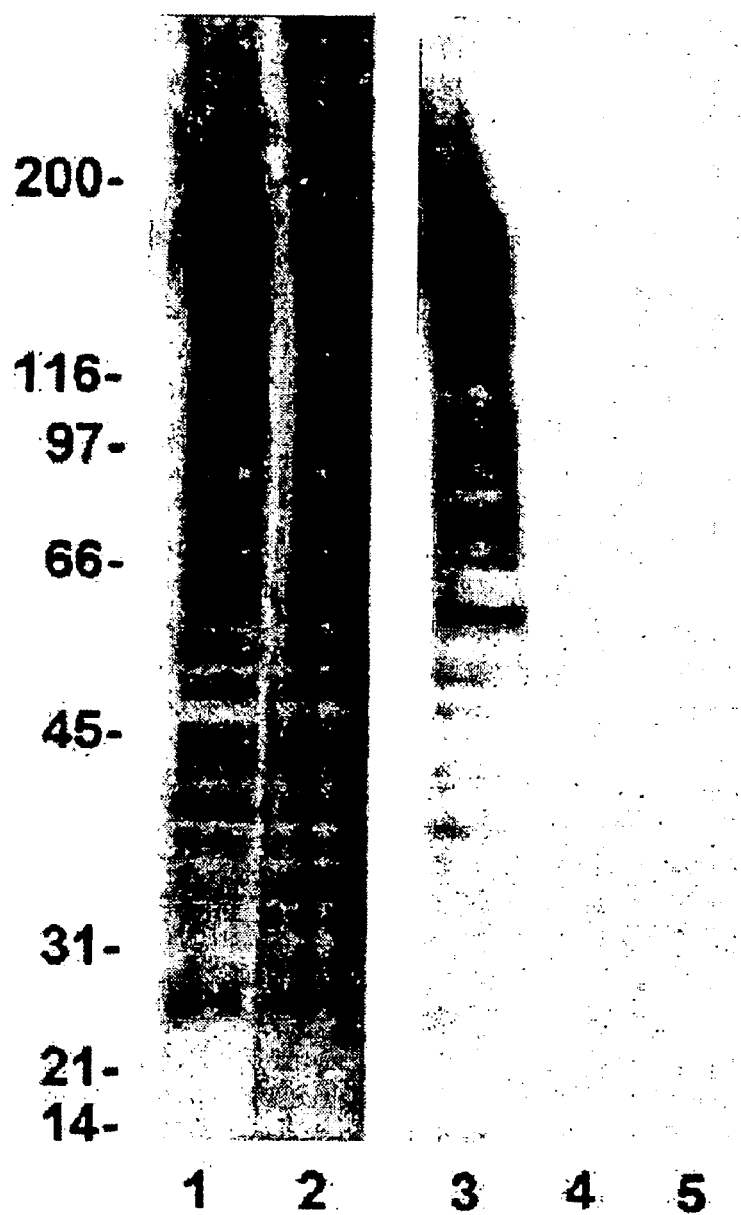
FIG. 2 shows an immunoblot of EGF stimulated A431 cell extracts probed with conditioned media from COS cells transfected with 4G 10 hybridoma light chain and His-tagged heavy chain cDNAs. Lane 1, HC clone-3His and LC clone-11; Lane 2, HC clone-7His and LC clone-11; Lane 3, native 4G10 at 2 µg/ml; Lane 4, same as Lane 1 except for the addition of 50 mM phenylphosphate to the conditioned media used for primary antibody probing; Lane 5, same as Lane 2 except for the addition of 50 mM phenylphosphate to conditioned media used for primary antibody probing. Molecular weight markers in kilodaltons are indicated at the left.

The ability of the cloned HC and LC cDNAs to produce a secreted functional recombinant monoclonal antibody capable of recognizing phosphotyrosine containing proteins was initially examined by transiently transfecting African green monkey COS cells. HC and LC plasmids were transiently transfected into COS cells using the transfection agent Lipofectamine (Life Technologies, Gaithersburg, Md.) and the conditioned media collected 3 to 5 days later. The human epidermoid carcinoma cell line A431 was used to monitor the ability of the recombinant antibody to specifically recognize phosphotyrosine containing cellular proteins. A431 overexpress the Epidermal Growth Factor receptor (EGFr) and upon stimulation with EGF there is a marked increase in phosphorylation of tyrosine residues in the cytoplasmic signal transducing region of the EGFr as well as many other proteins that are components of the signaling cascade downstream of the EGFr (Hunter, T. and Cooper, J. A., Cell 3:741–52 (1981); Goldkorn, T. et al., J. Biol. Chem., 266(24):16092–7 (1991); Moghal, N., et al., Curr Opin Cell Biol. 2:190–6 (1999). The ability of the secreted recombinant 4G10 monoclonal antibody to recognize phosphotyrosine proteins was determined by immunoblotting total protein cell lysates of EGF stimulated A431 cells. FIGS. 1 and 2 clearly demonstrate that the conditioned media from COS cells co-transfected with LC and HC plasmids or LC and HC His-tagged plasmids recognized the same complex pattern of phosphotyrosine containing proteins that native 4G11 recognizes. Conditioned media from empty vector transfection controls and secondary antibody alone did not recognize any protein bands from the EGF stimulated A431 immunoblots. Furthermore, the addition of 50 mM phenylphosphate, a competitive inhibitor of phosphotyrosine binding to 4G 10, completely blocked recognition of A431 phosphotyrosine containing proteins.

In order to produce sufficient quantities of r4G10 for commercial sale, stable transfected Chinese Hamster Ovary (CHO) cell lines were generated. CHO cells are routinely used for making recombinant monoclonal antibodies (Trill, J. R. et. al., *Current Opinion in Biotechnology*, 6:553–560, 1995) and several high expressing cell lines were generated by transfection and selection by the method of Page and Sydenham (*Biotechnology*, 9:64–68, 1991). Briefly, the mouse dihydrofolate reductase (DHFR) cDNA (Subramani, S. et. al., *Mol. Cell. Biol.* 1:854–864) was cloned into the LC expression plasmid such that it replaced the Neomycin resistance cassette of pcDNA3.1 whereas the HC expression plasmid retained the Neomycin resistance cassette. After co-transfection transformants were selected for the double phenotype of dhfr$^+$/neo resistance and colonies were pooled. To select for clones that produced high amounts of recombinant antibody, the pooled clones were cultured in the presence of $10^{-7}$ M methotrexate, a competitive inhibitor of DHFR that allows for amplification of the integrated linked HC and LC expression cassettes. Individual clones that survived methotrexate were expanded and secreted antibody production measured by an anti-IgG ELISA. High r4G10 antibody producing clones were subjected to a further round of amplification by culturing in the presence of $10^{-6}$ M methotrexate and again clones secreting high levels of antibody were identified by the anti-IgG ELISA.

The high producing his-tagged r4G10 CHO clones were cultured in spinner flasks or bioreactors and conditioned media pooled for antibody purification. Approximately 400 ml of CHO-4G10 conditioned media was equilibrated by adding 100 ml of 2.5 M NaCl, Sodium Phosphate pH 8.0. A 12 ml Nickel-IDA column was equilibrated with 5 column volumes of 0.5 M NaCl, 0.05 M Sodium Phosphate pH 8.0 before the sample was passed over the column once. The column was washed with 30 column volumes of 0.5 M NaCl, 0.05 M Sodium Phosphate pH 8.0 and then washed with 5 column volumes of 90% Buffer A (0.5 M NaCl, 0.05 M Sodium Phosphate pH 8.0) and 10% Buffer B (0.5 M NaCl, 0.05 M Sodium Phosphate pH 8.0 0.5 M Imidazole). Recombinant 4G10 was eluted with a 5 column volume linear gradient starting with 90% Buffer A, 10% Buffer B finishing with 100% Buffer B. Eluted fractions were collected in 2 ml tubes containing 50 mM EDTA pH 8.0 to 5% of their programmed volume. As determined by an IgG ELISA, the antibody eluted in the range of 150–250 mM Imidazole and was greater than 95% pure as assessed by SDS-PAGE. Peak fractions were pooled, dialyzed, concentrated, and buffer conditions adjusted to 1× PBS, pH 7.5, 0.02% sodium azide before the addition of glycerol to 30%.

Figure 3:
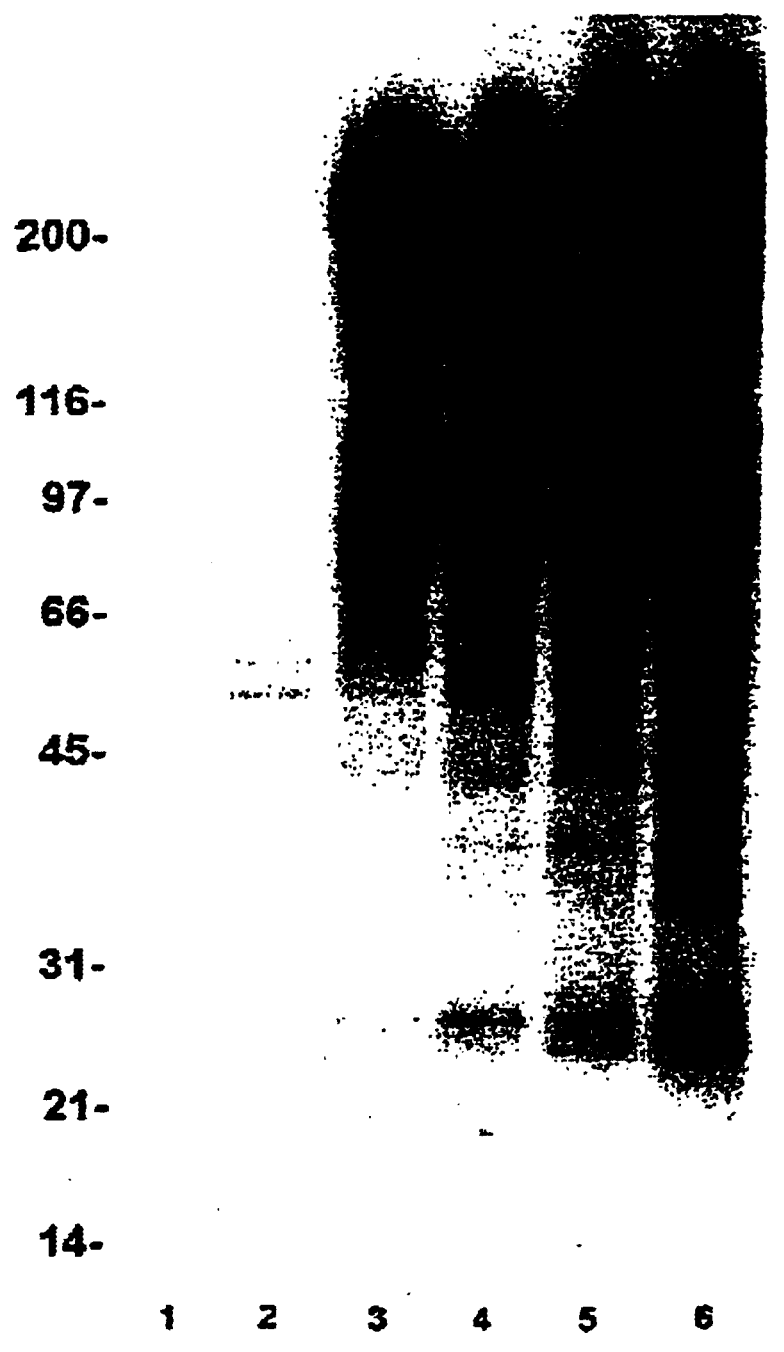
Figure 4:
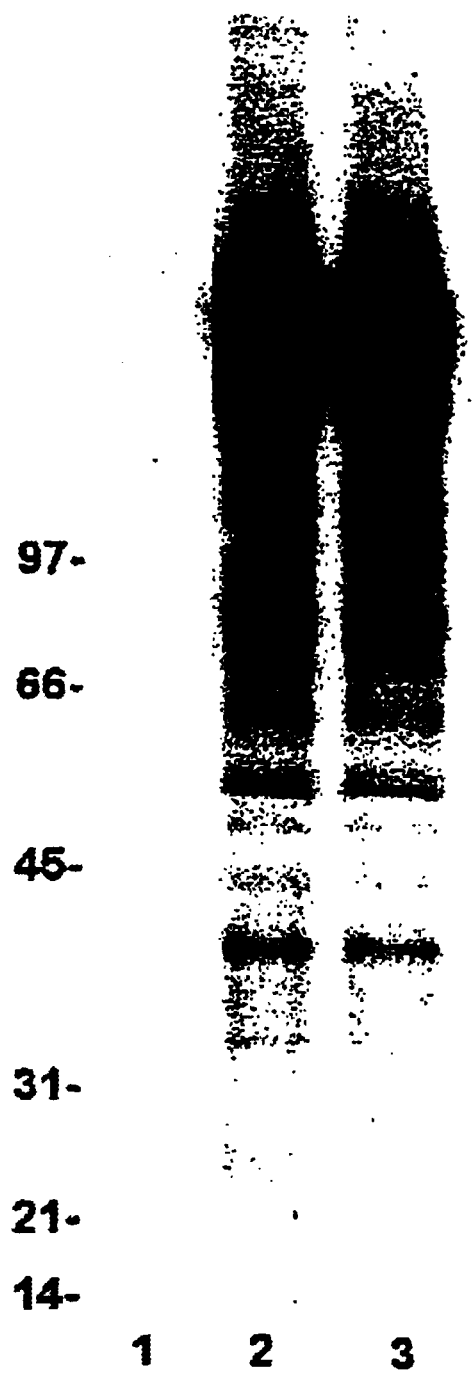
FIG. 4 shows an immunoblot of EGF stimulated A431 cell extracts probed with 1 µg/ml purified recombinant 4G10 stored under different conditions. Lane 1, No primary antibody. Lane 2, Recombinant 4G10 frozen at −20° C. in 30% glycerol. Lane 3, Recombinant 4G10 stored at 4° C. Molecular weight markers in kilodaltons are indicated at the left.

Purified r4G10 was analyzed for its ability to recognize phosphotyrosine containing proteins. FIG. 3 demonstrates that the ability of r4G10 to immunoprecipitate phosphotyrosine containing proteins from EGF stimulated A431 cell lysates is comparable to native 4G10. FIG. 4 demonstrates that probing an immunoblot of A431 cell lysates an with purified r4G10 recognizes the unique pattern of phosphotyrosine containing proteins that is recognized by native 4G10.

Determination of 4G10 Purity by SDS Page

His-tagged recombinant 4G10 was purified as described and subjected to SDS-PAGE for determination of the number of polypeptides and their approximate molecular weights. A PAGE-ONE 4/20% polyacrylamide gel (Owl Separation Systems, Portsmouth, N.H.) was used for electrophoretic separation of proteins according to the method of Laemmli (Laemmli, U.K., 1970, Nature, 227, p680). Protein samples were prepared by adding 6 µl of each protein (1 µg/µl) to 4 µl dH$_2$O (distilled water) and 10 µl 2× Sample Buffer (Sigma, St. Louis, Mo.). Samples were boiled for 5 min, centrifuged briefly, and 20 µl of each boiled sample was loaded on the gel. The gel was electrophoresed using 800 ml of running buffer (3 gr/L Tris base, 14.4 gr/L Glycine, 1 g/L SDS) with 40 mAmps of current for 2 hrs. The gel was then removed from its casing and rocked in dH$_2$O for 5 min. Bio-Safe Coomassie (Bio-Rad Laboratories, Hercules, Calif.) was then used to stain the gel. Staining consisted of rocking the gel in the Coomassie for 30 min. The subsequent destaining consisted of three, 10 min. washes with dH$_2$O, while gently rocking the gel. Finally, the gel was dried between two sheets of cellulose on a gel drying frame (Diversified Biotech, Boston, Mass.).

The antibody of the present invention was purified according to the already described procedure. For the His-tagged recombinant 4G10 the purification procedure is performed under pH neutral conditions without exposing the antibody to acidic solutions that are detrimental to antibody phosphotyrosine binding activity and represents a novel purification approach. This method, employing neutral or near-neutral pH, is also useful in purifying other antibodies as well as the 4G10-specific antibody of the present invention. The non-tagged antibody is prepared from the tagged antibody by removal of the tag or by Protein A affinity chromatography as is currently done for the native 4G10 product. A convenient protocol follows.

Purification of 4G10 by Protein A Affinity Chromatography

Two hundred ml of clarified Conditioned medium is loaded twice on to a 5 ml packed volume Protein A column at a flow rate of 2 ml/min. The column is then washed with 400 ml of PBS and eluted with 15 ml of pH 2.7 Elution buffer (50 mM Glycine, pH 2.7) and 1 ml fractions that have been pre-spiked with 100 microliters of neutralization buffer (1M Tris, 1.5M NaCl, 1 mM EDTA, 0.5% sodium azide) are collected. Fractions are immediately mixed after collecting to ensure prompt neutralization. The antibody peak fractions are pooled and diluted to 1 mg/ml prior to use.

Additional General References:
1. Cohen, B., et al., *Proc. Natl. Acad. Sci. USA.* 87: 4458–4462, 1990.
2. Druker, B. J., et al., *New Eng. J. Med.* 321: 1383–1391, 1989.
3. Kanakura, Y., et al., *J. Biol. Chem.* 266: 490–495, 1991.

What is claimed is:

1. An isolated recombinant monoclonal antibody comprising two light chain components and two heavy chain components wherein each of said heavy chain components contains SEQ ID NO: 4 and each of said light chain components contains SEQ ID NO: 5.

2. The isolated recombinant monoclonal antibody of claim 1 wherein said heavy chain components exhibit a single band on gel electrophoresis.

3. The isolated recombinant monoclonal antibody of claim 1 wherein said recombinant monoclonal antibody of claim 1 wherein said recombinant monoclonal antibody further comprises a histidine tag.

4. The isolated recombinant monoclonal antibody of claim 3 wherein said heavy chain components exhibit a single band on gel electrophoresis.

5. The isolated recombinant monoclonal antibody of claim 3 wherein said histidine tag is part of a heavy chain component of said antibody.

6. The isolated recombinant monoclonal antibody of claim 1 wherein recombinant monoclonal antibody does not react with phosphoserine or phosphothreonine.

7. The isolated recombinant monoclonal antibody of claim 5 wherein said heavy chain component containing said histidine tag the amino acid sequence of SEQ ID NO: 6.

* * * * *